United States Patent
Takemoto et al.

(10) Patent No.: US 10,551,359 B2
(45) Date of Patent: Feb. 4, 2020

(54) SAMPLE VAPORIZATION UNIT AND GAS CHROMATOGRAPH

(71) Applicant: Shimadzu Corporation, Kyoto (JP)

(72) Inventors: Hajime Takemoto, Kyoto (JP); Yoshihiko Ide, Kyoto (JP); Takahiro Saeki, Kyoto (JP); Ryo Takechi, Kyoto (JP); Yuki Komori, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 316 days.

(21) Appl. No.: 15/550,435

(22) PCT Filed: Feb. 16, 2015

(86) PCT No.: PCT/JP2015/054156
§ 371 (c)(1),
(2) Date: Dec. 20, 2017

(87) PCT Pub. No.: WO2016/132439
PCT Pub. Date: Aug. 25, 2016

(65) Prior Publication Data
US 2018/0128786 A1 May 10, 2018

(51) Int. Cl.
*B01D 53/02* (2006.01)
*G01N 30/12* (2006.01)
(Continued)

(52) U.S. Cl.
CPC ....... *G01N 30/12* (2013.01); *B05C 17/00506* (2013.01); *B05C 17/00516* (2013.01);
(Continued)

(58) Field of Classification Search
CPC ........ B05C 17/00506; B05C 17/00516; B65D 41/28; G01N 2030/025; G01N 2030/126;
(Continued)

(56) References Cited

U.S. PATENT DOCUMENTS

| | | |
|---|---|---|
| 6,216,340 B1 | 4/2001 | Fassbind et al. |
| 2001/0013169 A1 | 8/2001 | Fassbind et al. |

(Continued)

FOREIGN PATENT DOCUMENTS

| | | |
|---|---|---|
| EP | 2 767 301 A1 | 8/2014 |
| JP | H05-4006 U | 1/1993 |

(Continued)

OTHER PUBLICATIONS

Search Report dated Dec. 19, 2018 in corresponding European Application No. 15882543.0; 7 pages.

(Continued)

*Primary Examiner* — Christopher P Jones
(74) *Attorney, Agent, or Firm* — Maier & Maier, PLLC

(57) ABSTRACT

A housing is provided with an internal space for accommodating an insert and a cylindrical cap attachment part provided, at the distal end surface thereof, with an opening part communicating with the internal space. An inclined groove that is inclined from the distal end side to the proximal end side of the cap attachment part along the circumferential direction of the cap attachment part is provided on the outer circumferential surface of the cap attachment part. A cap fixing part for attaching a seal cap to the cap attachment part has a cap holding part for holding the outer peripheral surface of the seal cap and an elastic part connected to the cap holding part. The elastic part is provided with a protrusion that is fit into the inclined groove of the outer peripheral surface of the cap attachment part.

11 Claims, 7 Drawing Sheets

(51) Int. Cl.
*G01N 30/18* (2006.01)
*B05C 17/005* (2006.01)
*B65D 41/28* (2006.01)
*G01N 30/16* (2006.01)
*G01N 30/02* (2006.01)
*G01N 35/04* (2006.01)

(52) U.S. Cl.
CPC ............ *B65D 41/28* (2013.01); *G01N 30/16* (2013.01); *G01N 30/18* (2013.01); *G01N 2030/025* (2013.01); *G01N 2030/126* (2013.01); *G01N 2035/0405* (2013.01)

(58) Field of Classification Search
CPC ........... G01N 2030/0405; G01N 30/12; G01N 30/16; G01N 30/18
See application file for complete search history.

(56) References Cited

U.S. PATENT DOCUMENTS

| | | |
|---|---|---|
| 2004/0155045 A1 | 8/2004 | Wild et al. |
| 2006/0065122 A1 | 3/2006 | Song et al. |
| 2007/0090079 A1 | 4/2007 | Keller |

FOREIGN PATENT DOCUMENTS

| | | |
|---|---|---|
| JP | H11-166933 A | 6/1999 |
| JP | 2004-203489 A | 7/2004 |
| JP | 2005-5972 A | 1/2005 |
| JP | 4819462 B2 | 4/2006 |
| JP | 3129007 U | 2/2007 |
| JP | 2007-504058 A | 3/2007 |
| JP | 2007504058 A | 3/2007 |
| JP | 2009-92672 A | 4/2009 |
| JP | 2009092672 A | 4/2009 |
| JP | 4819462 B2 | 11/2011 |
| WO | 2015/004757 A1 | 1/2015 |

OTHER PUBLICATIONS

International Search Report dated Apr. 28, 2015 of corresponding application No. PCT/JP2015/054156; 2 pgs.

Japanese Office Action dated Mar. 13, 2018, in connection with corresponding JP Application No. 2017-500158 (6 pgs., including English translation).

Chinese Office Action dated Sep. 30, 2019, in connection with corresponding CN Application No. 201580078846.X (13 pgs., including machine-generated English translation).

SAMPLE VAPORIZATION UNIT AND GAS CHROMATOGRAPH

TECHNICAL FIELD

The present invention relates to a sample vaporization unit which has a sample vaporization chamber for vaporizing a sample injected by a sampler and feeds the sample vaporized in the sample vaporization chamber to an analysis column, and a gas chromatograph equipped with the sample vaporization unit.

BACKGROUND ART

In general, a gas chromatograph is provided with a sample vaporization unit for vaporizing the sample and feeding the sample to the analysis column. When describing one example of the sample vaporization unit, the sample vaporization unit has a housing, a space serving as a sample vaporization chamber is provided inside the housing, and a sample injection port for injecting the sample into the sample vaporization chamber is provided in the upper part of the housing. The lower part of the sample vaporization chamber is connected to an analysis column, and a carrier gas is introduced from the upper part of the sample vaporization chamber. The sample vaporization chamber is heated to a high temperature, and the liquid sample injected into the sample vaporization chamber is vaporized by heat and sent to the analysis column by the carrier gas.

A cylindrical insert made of quartz glass or the like is accommodated in the sample vaporization chamber inside the housing, and the sample injected from the sample injection port is vaporized inside the insert. Since the sample is configured to be vaporized inside the insert, the sample gas can be introduced into the analysis column, without coming into contact with the metal inner wall of the sample vaporization chamber.

Since the insert is in direct contact with the sample, the insert is a component that is easily stained due to adhesion of vaporized residues of the sample or the like. For this reason, the insert is accommodated in the sample vaporization chamber in a removable state so that the insert can be periodically exchanged or cleaned (see Patent Document 1).

Generally, an opening part communicating with the sample vaporization chamber is provided on the upper surface of the housing, and the opening part is sealed by attaching the seal cap in a state in which the opening part nips the O-ring. The sample injection port for injecting the sample by sticking a sample injecting needle is provided in the seal cap. Inside the seal cap, a septum for closing the sample injection port again after the sample injecting needle has been extracted is provided.

As a structure for attaching the seal cap to the housing, a structure is generally adopted in which a screw provided on the housing side and a screw provided on the seal cap side are screwed together and the seal cap is turned and tightened. However, with such a structure, when replacing the insert, it is necessary to turn the seal cap using a tool such as a spanner. However, since there is a pipe or the like for introducing the carrier gas around the sample injection port, it is difficult to turn the tool, and the task is not easy. Therefore, a mechanism capable of facilitating attachment and detachment of the seal cap without using a tool is desired.

As a mechanism for solving the above problem, a mechanism is suggested in which a protrusion is provided on the housing (a lower assembly) side, an inclined surface for hooking the protrusion of the housing side is provided on the seal cap (upper assembly) side, and the protrusion of the housing side is hooked to the inclined surface of the seal cap side to turn the seal cap and raise the protrusion along the inclined surface, thereby attaching the seal cap to the housing (see Patent Document 2).

CITATION LIST

Patent Document

Patent Document 1: JP-A-2009-92672
Patent Document 2: Japanese Patent No. 4,819,462

SUMMARY OF THE INVENTION

Technical Problem

In the sample vaporization unit, in addition to facilitating the work of fixing the seal cap to the housing, it is also important to reliably maintain the airtightness of the sample vaporization chamber when the seal cap is fixed to the housing. In the sample vaporization unit of the related art, when the seal cap is fixed to the housing, in some cases, the tightening of the seal cap is weakened and the airtightness of the sample vaporization chamber is not sufficiently maintained.

Thus, an object of the invention is to facilitate attachment and detachment work of the seal cap of the sample vaporization unit and to reliably ensure airtightness of the sample vaporization chamber when fixing the seal cap.

Solution to Problem

An embodiment of a sample vaporization unit according to the invention includes an insert, a housing, a seal cap, and a cap fixing part. The housing has an internal space which accommodates the insert, and a cylindrical cap attachment part provided with an opening part communicating with the internal space on a distal end side thereof. An inclined groove is formed on an outer peripheral surface of the cap attachment part, the inclined groove being inclined from the distal end side toward a proximal end side of the cap attachment part along a circumferential direction, and having a start point at a position closest to the distal end side of the cap attachment part, and an end point at a position closest to the proximal end side of the cap attachment part. The seal cap is detachably attached to the cap attachment part of the housing to seal the opening part.

The cap fixing part attaches the seal cap to the cap attachment part. The cap fixing part has a cap holding part engaged with the seal cap to be movable in the circumferential direction on the outer peripheral surface, and an elastic part provided integrally with the cap holding part. The elastic part has a protrusion fitted into the inclined groove of the outer peripheral surface of the cap attachment part. The cap fixing part is rotatably attached to the cap attachment part so that the protrusion slides along the inclined groove inside the inclined groove. The elastic part of the cap fixing part has a spring property which generates an elastic force of pressing the cap holding part toward the opening part so that the seal cap seals the opening part when the protrusion approaches the end point of the inclined groove.

An embodiment of a gas chromatograph according to the invention includes the aforementioned sample vaporization unit, an analysis column connected to an outlet part of the sample vaporization unit to separate a sample having passed through the sample vaporization unit, and a detector which detects the sample separated by the analysis column.

Advantageous Effects of the Invention

In one embodiment of the sample vaporization unit according to the invention, the inclined groove is formed on the outer peripheral surface of the cap attachment part provided on the housing side, and when the protrusion of the cap fixing part holding the seal cap is fitted into the inclined groove to turn the cap fixing part and the protrusion is made to slide to the end point of the inclined groove, the cap fixing part generates an elastic force which presses the cap holding part toward the opening part side so that the seal cap seals the opening part. Thus, the seal cap can be easily attached to the cap attachment part of the housing by merely turning the cap fixing part until the protrusion approaches the end point of the inclined groove, and the opening part can be reliably sealed. There is an end point in the inclined groove, and when the cap fixing part is turned until the protrusion approaches its end point, the amount of stroke between the cap holding part and the protrusion can always be kept constant. Thus, constant sealing property can always be obtained in the opening part of the housing.

Since the gas chromatograph of the invention includes the sample vaporization unit of the invention, the work of attaching and detaching the insert of the sample vaporization unit is facilitated, and the efficiency of the maintenance work is improved.

MODE FOR CARRYING OUT THE INVENTION

Figure 1:
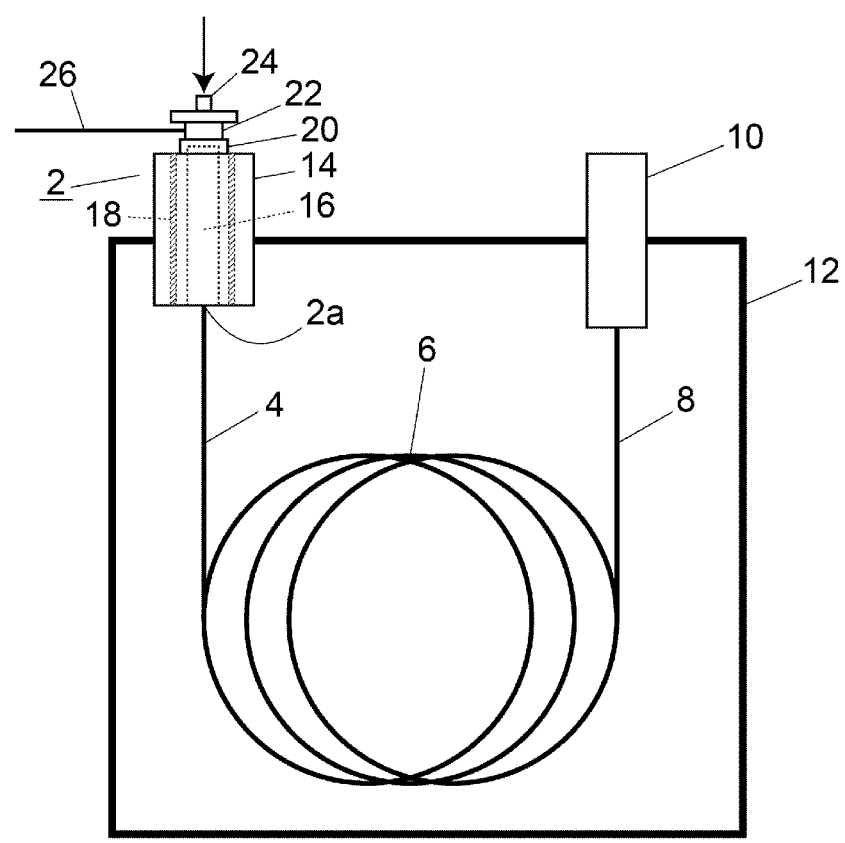
FIG. 1 is a configuration diagram schematically illustrating an embodiment of a gas chromatograph.

As a further preferred embodiment of a sample vaporization unit according to the invention, it is possible to adopt an example in which, when a protrusion moves from a start point to an end point side of an inclined groove, at a position of the end point of the inner surface of the inclined groove which slides with the protrusion, a hollow is provided which fits the protrusion to the distal end side of the cap holding part to suppress the movement of the protrusion toward the start point side. As a result, the protrusion sliding up to the end point of the inclined groove is freely moved to the start point side of the inclined groove by the elastic force of the elastic part of the cap fixing part, and the fastening of the seal cap is prevented from loosening.

It is preferable that a plurality of inclined grooves be uniformly provided in the circumferential direction of the cap attachment part on the outer peripheral surface of the cap attachment part. Then, the seal cap can be uniformly pressed toward the opening part side in the circumferential direction, and the opening part sealed by the seal cap can be more reliably sealed.

The cap holding part and the elastic part of the cap fixing part may be integrally formed. Then, it is possible to use an integrally molded means such as metal injection molding (MIM) with excellent appearance.

Also, depending on the material of the cap fixing part, particularly, the material of a spring material forming the elastic part, the material may be expensive and difficult to be machined in some cases. In that case, it is difficult to form the elastic part integrally with the cap holding part. In such a case, the cap holding part and the elastic part may be formed as separate bodies and connected to each other. By forming the elastic part which is a spring material as a separate part from the cap holding part, and thereafter, by connecting the cap holding part and the elastic part, even if the material is difficult to be machined, the cap fixing part is easily manufactured.

As a more specific embodiment of the sample vaporization unit according to the invention, the following configuration is adopted. That is, an annular elastic seal member surrounding the outer periphery of the insert is provided in the vicinity of the opening part in the internal space. On the opening part side of the inner wall surface of the internal space, an annular pedestal which supports an elastic seal member inserted from the opening part and surrounding the periphery of the insert is provided. A pressing part inserted into the internal space from the opening part to press the elastic seal member to the pedestal side is provided on the opening part side of the of the seal cap. When the protrusion of the cap fixing part reaches the end point of the inclined groove, the elastic seal member pressed against the pedestal side by the pressing part of the seal cap is deformed to seal the gap between the outer peripheral surface of the insert and the wall surface of the internal space.

It is preferable that a lever for driving the cap fixing part in the rotation direction be provided in the cap fixing part. Then, it is easy to turn the cap fixing part, and the work efficiency of attaching and detaching the seal cap from the housing is improved.

A flange part protruding in a flange shape in the circumferential direction is provided on the outer peripheral surface of the seal cap, and the cap holding part of the cap fixing part has an annular shape having an inner diameter smaller than the outer diameter of the flange part. It is preferable that the seal cap be pressed toward the opening part side by engaging the surface on the opening part side with the flange part. With such a configuration, the structure in which the cap fixing part holds the seal cap is simplified. Further, according to this configuration, since the cap holding part of the cap fixing part merely presses the seal cap toward the opening part, the cap fixing part can be freely turned with respect to the seal cap, and only the cap fixing part can be turned without turning the seal cap.

When a needle insertion part for inserting a sample injection needle toward the internal space is provided on the surface of the opposite side to the opening part of the seal cap, the seal cap preferably includes a septum made of a resilient material which is capable of penetrating by the needle inserted from the needle insertion part and closing the hole after extraction of the needle, on the side closer to the opening part side than the needle insertion part. Then, the airtightness after extracting the sample injection needle can be maintained.

The protrusion is preferably formed on the elastic part in consideration of the deflection of the elastic part so that the protrusion is perpendicular to the outer peripheral surface of the cap attachment part, when the relative displacement amount of the protrusion from the seal holding part becomes the maximum. Then, when the stress applied to the protrusion becomes the maximum, the protrusion is fitted into the inclined groove in a posture perpendicular to the outer peripheral surface of the cap attachment part. Therefore, it is possible to prevent large stress from acting only on a specific point of the protrusion, and to prevent wear or breakage of the protrusion.

An example of a gas chromatograph will be described with reference to FIG. 1.

The gas chromatograph of this embodiment includes a sample vaporization unit 2, an analysis column 6, a detector 10, and a column oven 12. A flow path 4 on one end side of the analysis column 6 is connected to the outlet part 2a of a lower end of the sample vaporization unit 2, and a flow path 8 on the other end side is connected to the detector 10. The analysis column 6 is accommodated in the column oven 12, and the sample vaporization unit 2 and the detector 10 are attached to the upper part of the column oven 12.

In the sample vaporization unit 2, a columnar insert 16 forming the sample vaporization chamber is accommodated in the internal space of the housing 14, and the internal space in which the insert 16 is accommodated is heated by the heater 18. An opening part 28 (see FIG. 2) communicating with the internal space for accommodating the insert 16 is provided on the upper surface of the housing 14, and the edge of the opening part 28 protrudes upward from the upper surface of the housing 14 in an annular shape to form a cap attachment part 20. A seal cap 22 is attached to the cap attachment part 20, and the opening part 28 is sealed with the seal cap 22. The seal cap 22 is provided with a needle insertion part 24 that opens upward and guides the sample injection needle descending from above to the internal space of the housing 14.

A pipe 26 is connected to the seal cap 22. The pipe supplies a carrier gas for feeding the sample gas vaporized in the sample vaporization chamber 6 to the analysis column 6. The carrier gas from the pipe 26 is introduced between the upper end portion of the insert 16 and the needle insertion part 24.

The sample to be analyzed is injected into the housing 14 by the needle inserted into the housing 14 via the needle insertion part 24, and is vaporized inside the insert 16 heated by the heater 18. The sample gas vaporized inside the insert 16 is introduced into the analysis column 6 by the carrier gas from the pipe 26, is separated for each component by the analysis column 6, and then, is detected for each component by the detector 10. Although not illustrated in this embodiment, in some cases, a detector such as a mass spectrometer may also be connected to the further downstream side of the detector 10. The invention is also applicable to such a gas chromatograph.

Next, the sample vaporization unit 2 will be described with reference to FIGS. 2 to 7.

Figure 2:
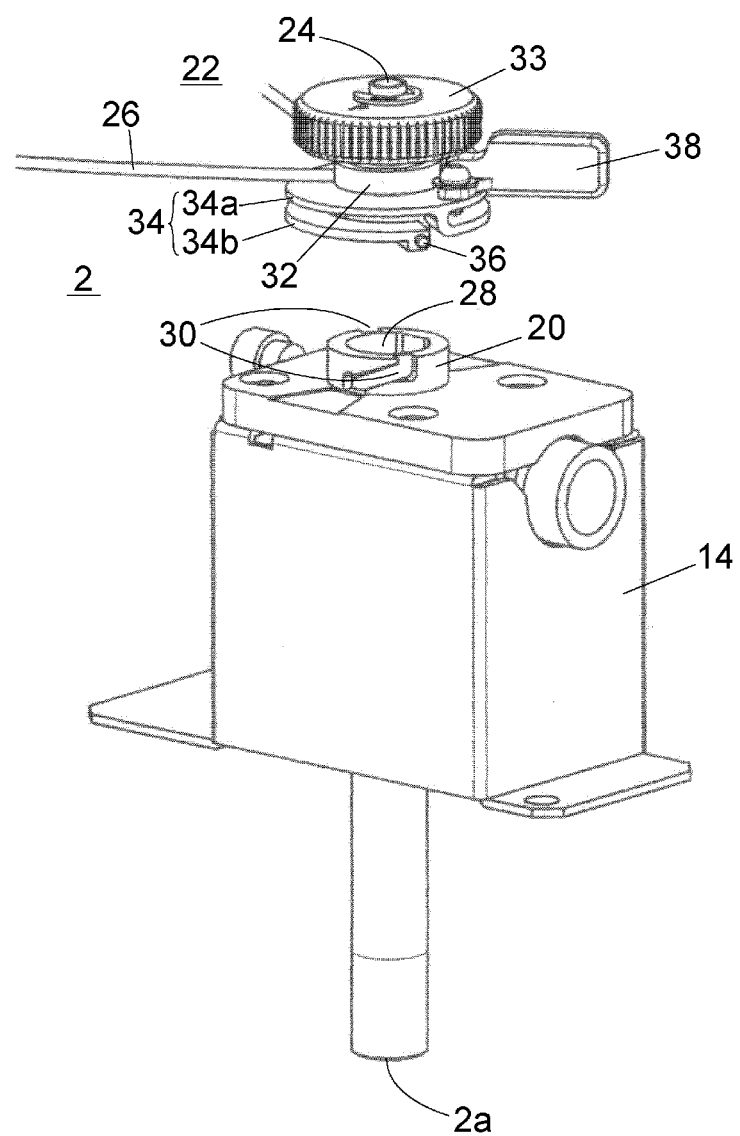
FIG. 2 is a perspective view illustrating an embodiment of a sample vaporization unit before attaching a seal cap.
Figure 3:
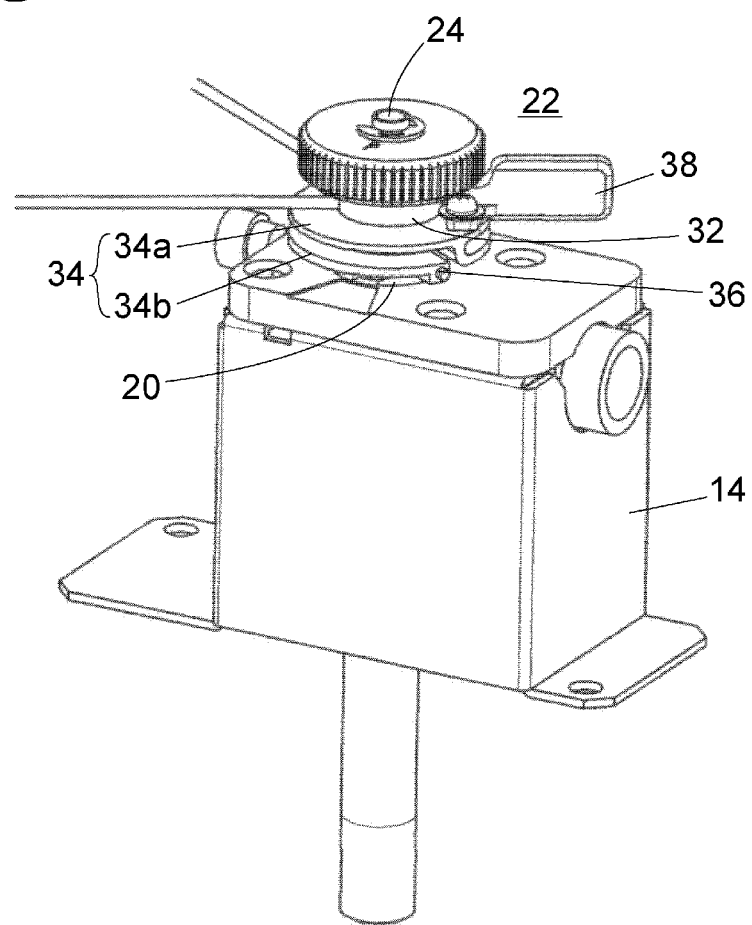
FIG. 3 is a perspective view of the same embodiment after attaching the seal cap.
Figure 4:
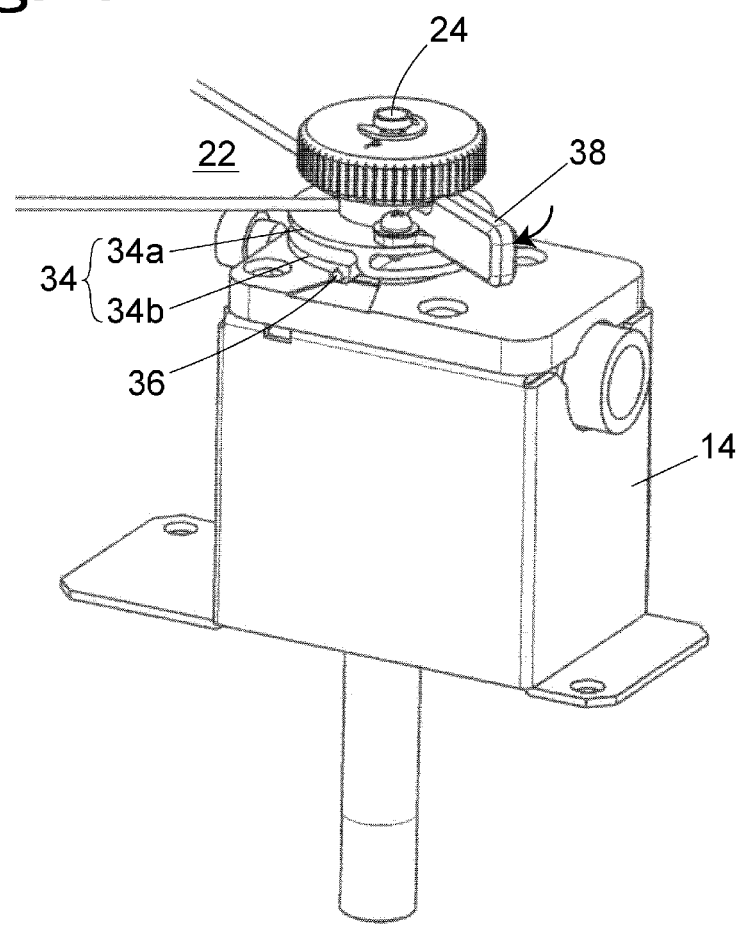
FIG. 4 is a perspective view of the same embodiment after fixing the seal cap.

As illustrated in FIGS. 2 to 4, the housing 14 of the sample vaporization unit 2 has a prismatic shape in this embodiment. Further, the shape of the housing 14 is not limited to a prismatic shape, but may be a cylindrical shape or another shape. The housing 14 includes a space 14a (see FIG. 5, hereinafter referred to as an internal space 14a) for accommodating the insert 16 therein. The internal space 14a includes a hole having a circular cross section and leading from the upper surface of the housing 14 to the lower outlet part 2a. The housing 14 is made of a metal material having good thermal conductivity. Although not represented in FIG. 2, the heater 18 (see FIG. 1) is embedded in the housing 14 to surround the internal space 14a, and the insert 16 accommodated in the internal space 14a is heated by the heater 18. The insert 16 is a cylindrical member made of quartz glass or the like.

The opening part 28 of the housing 14 is sealed with the seal cap 22. The seal cap 22 includes a cylindrical seal cap main body 32, and a disk-shaped septum cover 33 attached to the uppermost portion of the seal cap main body 32. The needle insertion part 24 is provided on the septum cover 33.

Figure 5:
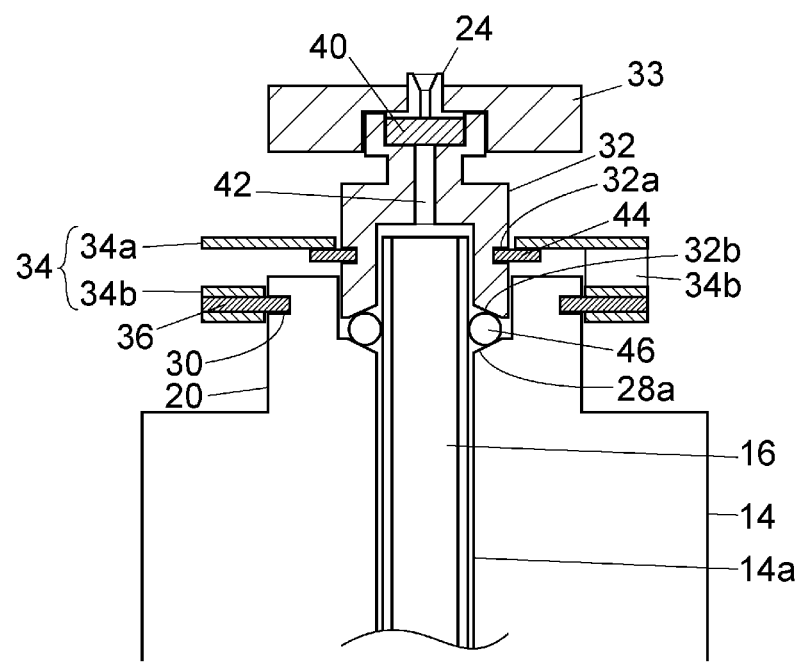
FIG. 5 is a cross-sectional view of the same embodiment.

As illustrated in FIG. 5, a septum 40 is disposed at the uppermost part of the seal cap main body 32, and the septum cover 33 is attached at the uppermost portion of the seal cap main body 32 so that the needle insertion part 24 is located above the septum 40. The sample injection needle inserted from the needle insertion part 24 is capable of penetrating through the septum 40, and the septum 40 closes a through-hole formed by the needle due to its elasticity after extracting the needle. The septum 40 is made of an elastic material such as natural rubber or silicone rubber. The sample is discharged from the distal end of the needle penetrating the septum 40 to the insert 16 side via the through-hole 42 at the center of the seal cap main body 32.

The edge of the opening part 28 on the upper surface of the housing 14 protrudes upward in an annular shape to form the cap attachment part 20. The seal cap 22 is fixed to the cap attachment part 20 by the cap fixing part 34. Inclined grooves 30 are provided at two symmetrical positions on the outer peripheral surface of the cap attachment part 20. The inclined grooves 30 are inclined along the circumferential direction of the cap attachment part 20 from the distal end side to the proximal end side of the cap attachment part 20. When the seal cap 22 is attached to the housing 14, the pin 36 (protrusion) of the cap fixing part 34 attached to the seal cap 22 is fitted into the inclined groove 30 and slides therein.

Figure 6A:
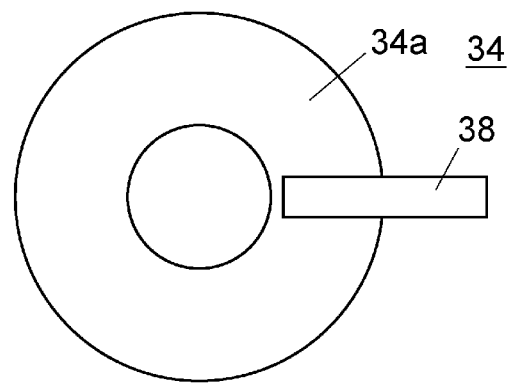
FIG. 6A is a plan view illustrating a cap fixture of the same embodiment.
Figure 6B:
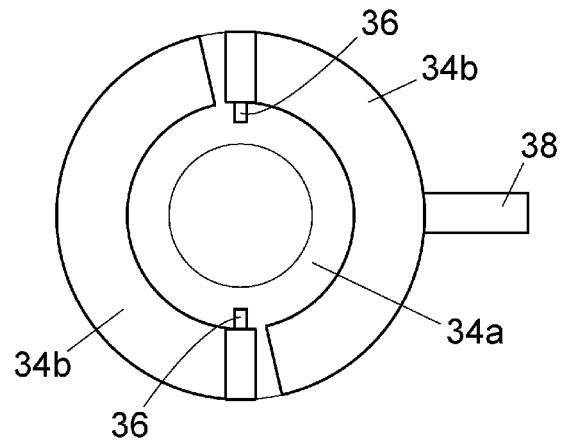
FIG. 6B is a bottom view illustrating the cap fixture of the same embodiment.
Figure 6C:
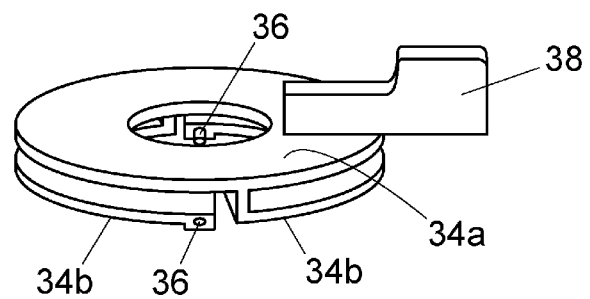
FIG. 6C is a perspective view illustrating the cap fixture of the same embodiment.

As illustrated in FIGS. 6A to 6C, the cap fixing part 34 includes a disk-shaped cap holding part 34a with a hole provided at the center, and two elastic parts 34b provided integrally with the cap holding part 34a on one side surface of the cap holding part 34a. When the side on which the elastic part 34b of the cap fixing part 34 is not provided is defined as a front side and the side on which the elastic part 34b is provided is referred to as a back side, the cap fixing part 34 is attached to the seal cap main body 32 so that its back side faces the housing 14 side.

The elastic part 34b of the cap fixing part 34 is provided at a certain interval from the cap holding part 34a to draw an arc along the peripheral edge of the cap holding part 34a. The proximal end of the elastic part 34b is integral with the cap holding part 34a, but the distal end thereof is a free end. That is, the elastic part 34b is a cantilever spring. A pin 36 protruding inward is provided at the distal end of the elastic part 34. The two elastic parts 34b have the same shape, and the pins 36 at their respective distal ends are disposed at positions opposite to each other. A lever 38 for holding and turning the cap fixing part 34 is provided in the cap holding part 34a.

In this embodiment, the cap holding part 34a and the elastic part 34b of the cap fixing part 34 are integrally formed by a manufacturing method such as shaving from the metal block or MIM. Further, the cap holding part 34a and the elastic part 34b may be formed as separate parts and then connected to each other. In this case, the materials of the cap holding part 34a and the elastic part 34b need not be the same.

The cap holding part 34a is engaged with the seal cap main body 32 to be movable in the circumferential direction of the outer peripheral surface thereof. As illustrated in FIG. 5, a horizontal groove 32a which is an annular recess provided in the circumferential direction is provided on the outer peripheral surface of the seal cap main body 32. A C-shaped retaining ring 44 is fitted to the horizontal groove 32a. The C-shaped retaining ring 44 is a C-shaped metal member having a notch in a part, and has an inner diameter substantially equal to the outer diameter of a portion of the seal cap main body 32 in which the horizontal groove 32a is provided, and an outer diameter larger than the outer diameter of the portion of the seal cap main body 32 in which the horizontal groove 32a is not provided. The C-shaped retaining ring 44 forms a flange part which projects in the circumferential direction from the outer peripheral surface of the seal cap main body 32. The inner diameter of the hole at the center of the cap holding part 34a of the cap fixing part 36 is larger than the outer diameter of the portion of the seal cap main body 32 in which the horizontal groove 32A is not provided, and is smaller than the outer diameter of the C-shaped retaining ring 44. The seal cap main body 32 is fitted into the center hole of the cap holding part 34a so that the C-shaped retaining ring 44 is located below the cap holding part 34a. Instead of the horizontal groove 32a and the C-shaped retaining ring 44, a flange part protruding in the circumferential direction from the outer peripheral surface of the seal cap main body 32 may be provided integrally with the seal cap 32.

In order to fix the seal cap 22 to the cap attachment part 20, the seal cap 22 is put on the cap attachment part 20 so that the pin 36 at the distal end of the elastic part 34b of the cap fixture 34 is fitted into the inclined groove 30 (the state of FIG. 3), and the cap fixture 34 is turned in one direction (the clockwise direction in FIG. 6A) to cause the pin 36 to slide along the inclined groove 30 (the state of FIG. 4).

Figure 7:
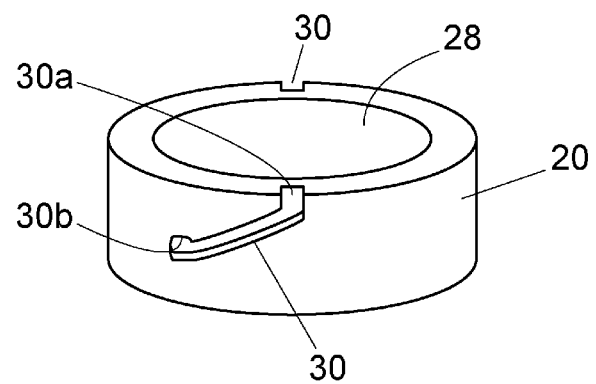
FIG. 7 is a perspective view illustrating a seal attachment part of the same embodiment.

As illustrated in FIG. 7, the inclined groove 30 of the cap attachment part 20 has a start point 30a on the distal end side (upper end side) of the cap attachment part 20, an end point 30b on the proximal end side (lower end side) of the cap attachment part 20, and is inclined along the outer peripheral surface of the cap attachment part 20 from the start point 30a to the end point 30b. A hollow is provided at the end point 30b of the inclined surface located on the distal end side of the cap attachment part 20 of the inclined groove 30. The hollow of the end point 30b is configured to fit the pin 36 reaching the end point 30b therein and prevent the pin 36 from moving to the start point 30a side. As a result, the pin 36 reaching the end point 30b does not arbitrarily move to the start point 30a side by the elastic force of the cap fixing part 34. When the pin 36 reaches the end point 30b, the pin 36 is fitted into the hollow to give a click feeling to the operator so that the operator can easily know completion of the work of attaching the seal cap 22 to the cap attachment part 20.

As illustrated in FIG. 5, an O-ring 46 (an elastic seal) for sealing a gap between the outer peripheral surface of the insert 16 and the inner wall surface of the internal space 14a is provided on the opening part side of the internal space 14a of the housing 14. The O-ring 46 is made of, for example, fluororubber or the like. An annular pedestal 28a inclined so that its inner diameter decreases toward the lower part is provided in the vicinity of the opening part 28 of the inner side wall of the housing 14, and the O-ring 46 is supported by the pedestal 28a. The seal cap main body 32 has a recess that accommodates the upper end of the insert 16 on the lower surface side, and a lower end portion thereof is accommodated in the opening part 28 to interpose the O-ring 46 between the lower end portion and the pedestal 28a. The annular lower end surface of the seal cap main body 32 is inclined so that the inner diameter increases toward the lower part contrary to the pedestal 28a.

When the seal cap 22 is put on the cap attachment part 20 so that the pin 36 of the cap fixing part 34 is aligned with the start point 30a of the inclined groove 30, the lower end of the seal cap main body 32 comes into contact with the O-ring 46. In this state, when the cap fixing part 34 is turned so that the pin 36 slides toward the end point 30b side of the inclined groove 30, the pin 36 descends to the proximal end side of the cap attachment part 20. Thus, the cap holding part 34a presses the C-shaped retaining ring 44 downward, thereby pressing the seal cap main body 32 downward. Since the cap holding part 34a is engaged with the C-shaped retaining ring 44, the cap fixing part 34 presses the seal cap main body 32 downward, while turning independently of the seal cap main body 32. Accordingly, it is possible to turn only the cap fixing part 34, without turning the seal cap 22.

The elastic part 34b of the cap fixing part 34 displaces the position of the pin 36 relative to the cap holding part 34a, and has a spring property which generates a restoring force depending on the amount of displacement when the position of the pin 36 is displaced relative to the cap holding part 34a. When the cap fixing part 34 is turned and the pin 36 reaches the end point of the inclined groove 30, the seal cap main body 32 is pressed in a direction of being pressed into the opening part 28 by the elastic force of the elastic part 34b, thereby deforming the O-ring 46 to such an extent that it is possible to completely prevent the entry of gas to the gap between the inner wall surface of the internal space 14a and the outer peripheral surface of the insert 16.

For example, in the cap fixing part 34, the cap holding part 34a has a thickness of about 1 mm and an outer diameter of about 30 mm, the elastic part 34b has a thickness of about 1.5 mm and an outer diameter of about 30 mm, and the gap between the cap holding part 34a and the elastic part 34b is about 2 mm. As the material of the cap fixing part 34, materials with tensile strength of about 1000 MPa, for example, stainless steel (e.g., SUS 630 or the like) subjected to precipitation hardening treatment or solution treatment, stainless steel as a spring material (e.g., SUS 301 CSP or SUS 304 CSP), alloy steel (e.g., SCM 420, SCM 445, SNCM 630, etc.), titanium alloys (e.g., Ti-6Al-4V (64 titanium) etc.), copper alloy (e.g., beryllium copper, phosphor bronze etc.) and the like are suitable.

With the above configuration, when the pin 36 of the cap fixing part 34 is fitted into the start point 30a of the inclined groove 30 and the cap fixing part 34 is turned until the pin 36 reaches the end point 30b, the attachment of the seal cap 22 to the housing 14 is completed. When the pin 36 reaches the end point 30b, the cap fixing part 34 does not further turn, and when the pin 36 reaches the end point 30b of the inclined groove 30, the pin 30 fits into the hollow provided at the end point 30b. Accordingly, the pin 36 is prevented from arbitrarily moving to the start point 30a side by the elastic force of the elastic part 34b of the cap fixing part 34. Therefore, when the seal cap 22 is attached to the housing 14, the seal cap main body 32 can always be pressed toward the housing 14 with a constant force.

Since the recess of the end point 30b is curved, when a force toward the start point 30a larger than the elastic force due to the elastic part 34b of the cap fixing part 34 is applied to the pin 36, the pin 36 is released from the hollow of the end point 30b and can move to the start point 30a side. That is, when detaching the seal cap 22 from the housing 14, an operator may apply the force to the cap fixing part 34 so as to turn the cap fixing part 34 in a direction opposite to the case where the seal cap 22 is attached to the housing 14 (a counterclockwise direction in FIG. 6A).

In this embodiment, since the cap fixing part 34 includes two disk members (the cap holding part 34a and the two elastic parts 34b), a surface area coming into contact with the outside air increases, and the cap fixing part 34 plays a role of heat dissipating fins. Thus, the seal cap 22 is quickly cooled.

Figure 8:
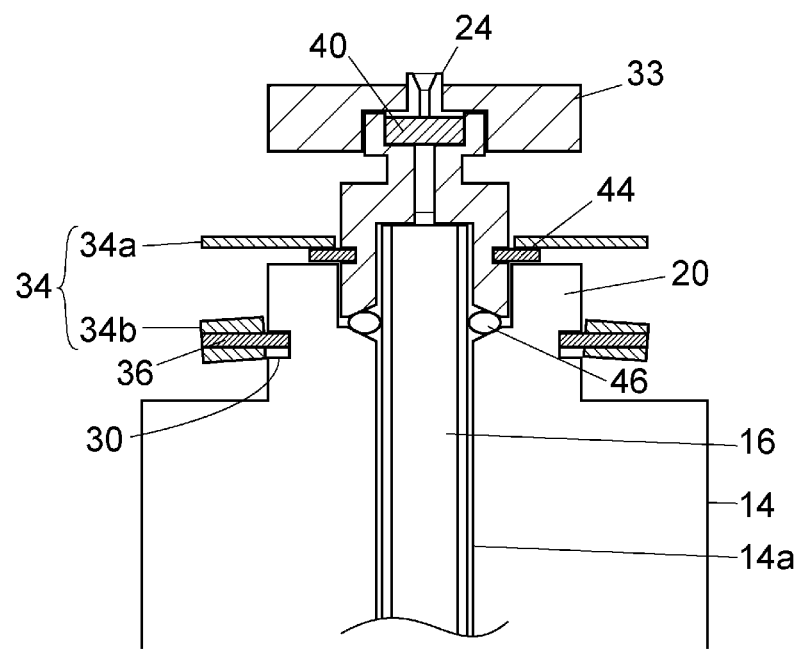
FIG. 8 is a cross-sectional view illustrating a modified example of the cap fixture in the same embodiment.

Further, since the elastic part 34b of the cap fixing part 34 has an arcuate shape, when the pin 36 slides inside the inclined groove 30 and the elastic part 34b is bent, the elastic part 34b is considered to be deformed such that the outside is lowered and the inside is directed upward. Therefore, in consideration of such deformation, as illustrated in FIG. 8, when the deformation amount of the elastic part 34b becomes the maximum, the pin 36 may be provided to be inclined at the distal end of the elastic part 34b so that the pin 36 is in a posture perpendicular to the outer peripheral surface of the cap attachment part 20. Then, when the stress applied to the pin 36 is the maximum, the pin 36 is in the state of being inserted perpendicularly to the inclined groove 30, and the entire upper surface of the pin 36 comes into contact with the wall surface of the inclined groove 30. Thus, it is possible to prevent concentration of stress, and to prevent breakage, abrasion, or the like of the pins 36.

REFERENCE SIGNS LIST

2 Sample vaporization unit
2a Sample vaporization unit outlet
4, 8 Flow path
6 Analysis column
10 Detector
12 Column oven
14 Housing
14a Internal space of housing
16 Insert
18 Heater
20 Cap attachment part
22 Seal cap
24 Needle insertion part
26 Pipe for carrier gas supply
28 Opening part
30 Inclined groove
30a Start point of inclined groove
30b End point of inclined groove
32 Seal cap main body
32a Horizontal groove
33 Septum cover
34 Cap fixing part
34a Cap holding part
34b Elastic part
36 Pin
38 Lever
40 Septum
42 Through-hole
44 C-shaped retaining ring
46 O-ring

The invention claimed is:
1. A sample vaporization unit comprising:
a tubular insert;
a housing having an internal space which accommodates the insert, and a cylindrical cap attachment part provided with an opening part communicating with the internal space on a distal end side thereof, at least one inclined groove being formed on an outer peripheral surface of the cap attachment part, the at least one inclined groove being inclined from the distal end side toward a proximal end side of the cap attachment part along a circumferential direction, and having a start point at a position closest to the distal end side of the cap attachment part, and an end point at a position closest to the proximal end side of the cap attachment part;
a seal cap detachably attached to the cap attachment part of the housing to seal the opening part; and
a cap fixing part which has a cap holding part engaged with the seal cap to be movable in the circumferential direction of the outer peripheral surface, and an elastic part connected to the cap holding part, the elastic part having a protrusion fitted into the at least one inclined groove of the cap attachment part, the cap fixing part being rotatably attached to the cap attachment part so that the protrusion slides along the at least one inclined groove inside the at least one inclined groove, the elastic part having a spring property for generating an elastic force of pressing the cap holding part toward the opening part so that the seal cap seals the opening part when the protrusion approaches the end point of the at least one inclined groove.

2. The sample vaporization unit according to claim 1, wherein a hollow is provided at a position of the end point of the inner surface of the at least one inclined groove that slides with the protrusion when the protrusion moves from the start point to the end point side of the at least one inclined groove, the hollow fitting the protrusion to the distal end side of the cap holding part to prevent movement of the protrusion toward the start point side.

3. The sample vaporization unit according to claim 1, wherein the at least one inclined groove comprises multiple inclined grooves that are uniformly provided on the outer peripheral surface of the cap attachment part in the circumferential direction of the cap attachment part.

4. The sample vaporization unit according to claim 1, wherein the cap holding part and the elastic part of the cap fixing part are integrally formed.

5. The sample vaporization unit according to claim 1, wherein the cap holding part and the elastic part of the cap fixing part are formed as separate bodies and connected to each other.

6. The sample vaporization unit according to claim 1, wherein an annular elastic seal member which surrounds the outer circumference of the opening part side of the insert is provided in the vicinity of the opening part in the internal space,
an annular pedestal which supports the elastic seal member inserted from the opening part to surround the periphery of the insert is provided on the opening part side of the inner wall surface of the internal space,
a pressing part which is inserted from the opening part into the internal space to press the elastic seal member toward the pedestal side is provided on the opening part side of the seal cap, and
when the protrusion of the cap fixing part reaches the end point of the at least one inclined groove, the elastic seal member pressed to the pedestal side by the pressing part of the seal cap deforms to seal a gap between the outer peripheral surface of the insert and the inner wall surface of the internal space.

7. The sample vaporization unit according to claim 1, wherein a lever for driving the cap fixing part in a rotation direction is provided in the cap fixing part.

8. The sample vaporization unit according to claim 1, wherein a flange part protruding in a flange shape in a circumferential direction is provided on an outer peripheral surface of the seal cap, and
the cap holding part of the cap fixing part has an annular shape having an inner diameter smaller than the outer diameter of the flange part, and a surface of the opening part side engages with the flange part to press the seal cap toward the opening part.

9. The sample vaporization unit according to claim 1, wherein the seal cap has a needle insertion part which inserts a sample injection needle toward the internal space on a surface of an opposite side to the opening part, and the seal cap includes a septum on a side closer to the opening part than the needle insertion part, the septum allowing the needle inserted from the needle insertion part to penetrate, and being made of an elastic material having elasticity to close the hole after extraction of the needle.

10. The sample vaporization unit according to claim 1, wherein the protrusion is provided in the elastic part so as to be perpendicular to the outer peripheral surface of the cap attachment part when the relative displacement amount of the protrusion from the seal holding part becomes maximum.

11. A gas chromatograph comprising:
the sample vaporization unit according to claim 1;
an analysis column which is connected to an outlet part of the sample vaporization unit to separate a sample having passed through the sample vaporization unit; and
a detector which detects the sample separated by the analysis column.

* * * * *